US00PP23518P3

(12) United States Plant Patent
Kardos

(10) Patent No.: US PP23,518 P3
(45) Date of Patent: Apr. 9, 2013

(54) ***LAGERSTROEMIA* PLANT NAMED 'PLUM MAGIC'**

(50) Latin Name: ***Lagerstroemia* L.**
Varietal Denomination: Plum Magic

(75) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 20 days.

(21) Appl. No.: 13/135,348

(22) Filed: Jul. 1, 2011

(65) Prior Publication Data

US 2013/0007933 P1 Jan. 3, 2013

(51) Int. Cl.
*A01H 5/00* (2006.01)

(52) U.S. Cl. ..... Plt./252

(58) Field of Classification Search ..... Plt./252
See application file for complete search history.

(56) References Cited

PUBLICATIONS

Plant Introductions, Inc.—promotional pages from Plant Introductions website showing color pictures of *Lagerstroemia* plants. 'Plum Magic' is shown on p. 2. Downloaded Jun. 23, 2011.
Page from Plant Introductions, Inc. catalog distributed at a tradeshow in Jan. 2011.

*Primary Examiner* — Susan McCormick Ewoldt
(74) *Attorney, Agent, or Firm* — Lathrop & Gage LLP

(57) ABSTRACT

A new and distinct cultivar of *Lagerstroemia* plant named 'Plum Magic', characterized by its compact, rounded to upright intermediate growth habit, plum-purple new growth, gray-green foliage in summer, fuchsia-pink flowers, and resistance to powdery mildew and *Cercospora* leaf spot.

4 Drawing Sheets

Genus and species of plant claimed: *Lagerstroemia* L.
Variety denomination: 'Plum Magic'.

BACKGROUND OF THE INVENTION

The present invention relates to a new and distinct cultivar of *Lagerstroemia* plant, botanically known as *Lagerstroemia* L., commonly known as crapemyrtle, and hereinafter referred to by the cultivar name 'Plum Magic'. 'Plum Magic' is grown primarily as an ornamental for landscape use and for use as a potted plant.

'Plum Magic' originated from open-pollinated seed of 'Gamad VI' (U.S. Plant Pat. No. 22,161) growing in Watkinsville, Ga. The cultivar 'Plum Magic' originated and was selected in a cultivated environment in Watkinsville, Ga. from the progeny of this open-pollination by continued evaluation for growth habit and foliage and flower characteristics.

Asexual reproduction of 'Plum Magic' by stem cuttings in Watkinsville, Ga. since 2008 has shown that all the unique features of this new *Lagerstroemia,* as herein described, are stable and reproduced true-to-type through successive generations of such asexual propagation.

SUMMARY OF THE INVENTION

Plants of the new cultivar 'Plum Magic' have not been observed under all possible environmental conditions. The phenotype may vary somewhat with changes in light, temperature, soil and rainfall without, however, any variance in genotype.

The following traits have been repeatedly observed and are determined to be unique characteristics of 'Plum Magic'. These characteristics in combination distinguish 'Plum Magic' as a new and distinct cultivar: 1. Compact, rounded to upright intermediate growth habit; 2. Plum-purple new growth; 3. Gray-green foliage in summer; 4. Fuchsia-pink flowers; 5. Resistance to powdery mildew and *Cercospora* leaf spot.

Plants of 'Plum Magic' differ from plants of the parent, 'Gamad VI', primarily in foliage and flower color. Plants of 'Gamad VI' have reddish new growth, green foliage in summer, and fuchsia flowers whereas plants of 'Plum Magic' have plum-purple new growth, gray-green foliage in summer, and fuchsia-pink flowers. Plants of 'Plum Magic' are similar to the cultivar 'White Chocolate' (not patented), but differ in the following ways. 'Plum Magic' has plum-purple new growth and fuchsia-pink flowers, whereas 'White Chocolate' has reddish purple new growth and white flowers. Plants of 'Plum Magic' are also similar to the cultivar 'Whit III' (U.S. Plant Pat. No. 10,319), but differ in that 'Plum Magic' has plum-purple new growth, gray-green mature foliage, and fuchsia-pink flowers, whereas 'Whit III' has ruby-red new growth, purplish green mature foliage, and bright red-purple flowers.

BRIEF DESCRIPTION OF THE DRAWINGS

The accompanying color photographs illustrate the flower and foliage characteristics and the overall appearance of 'Plum Magic', showing the colors as true as it is reasonably possible to obtain in color reproductions of this type. Colors in the photographs may differ slightly from the color values cited in the detailed botanical description which accurately describe the colors of the new *Lagerstroemia.*

DETAILED DESCRIPTION

Figure 1:
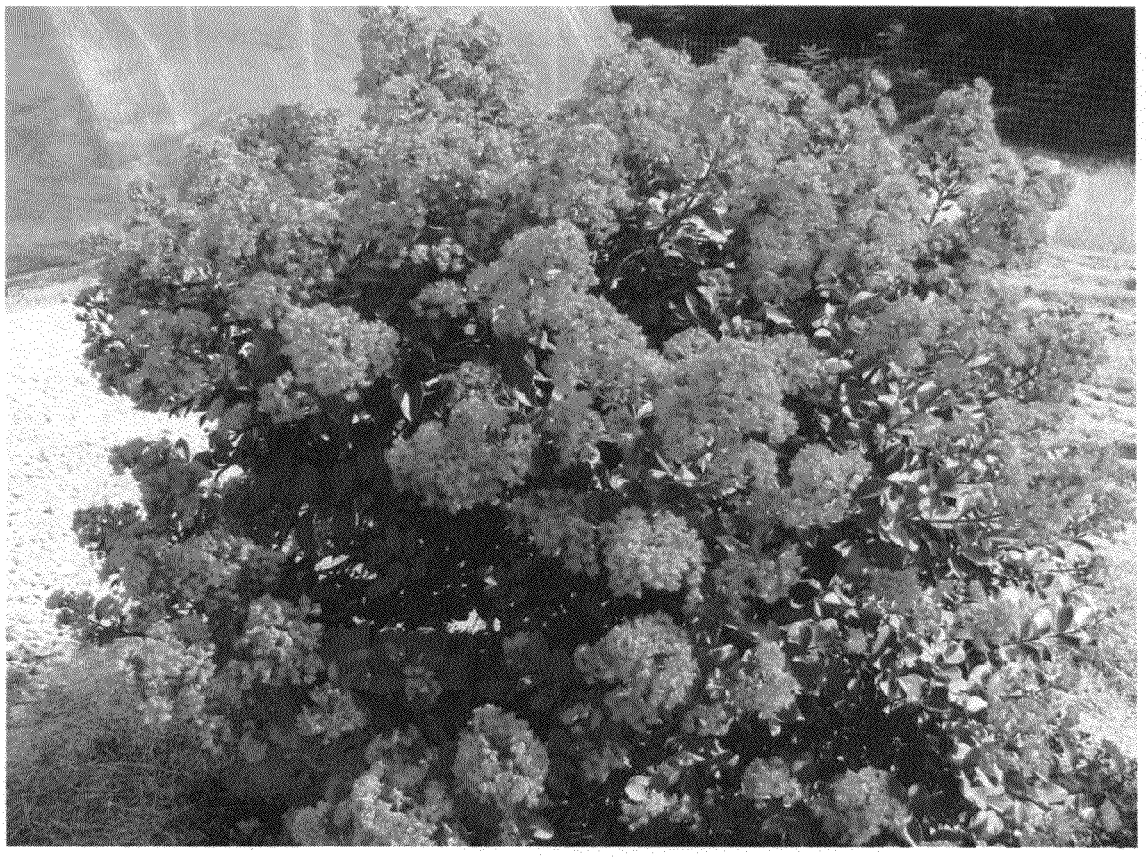
FIG. 1 illustrates the overall appearance of a mature plant of 'Plum Magic'.
Figure 2:
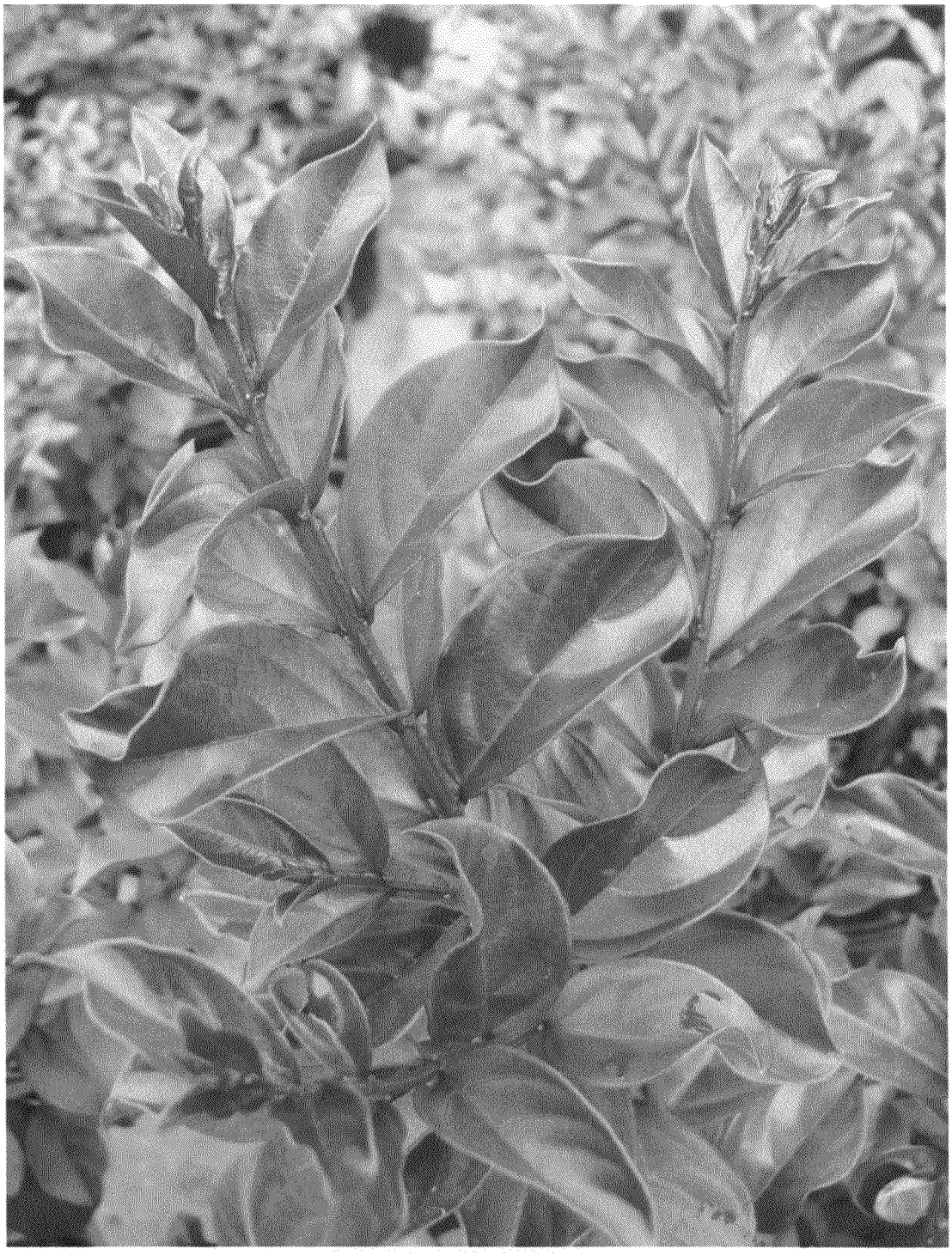
FIG. 2 illustrates a close-up view of the new growth of 'Plum Magic'.
Figure 3:
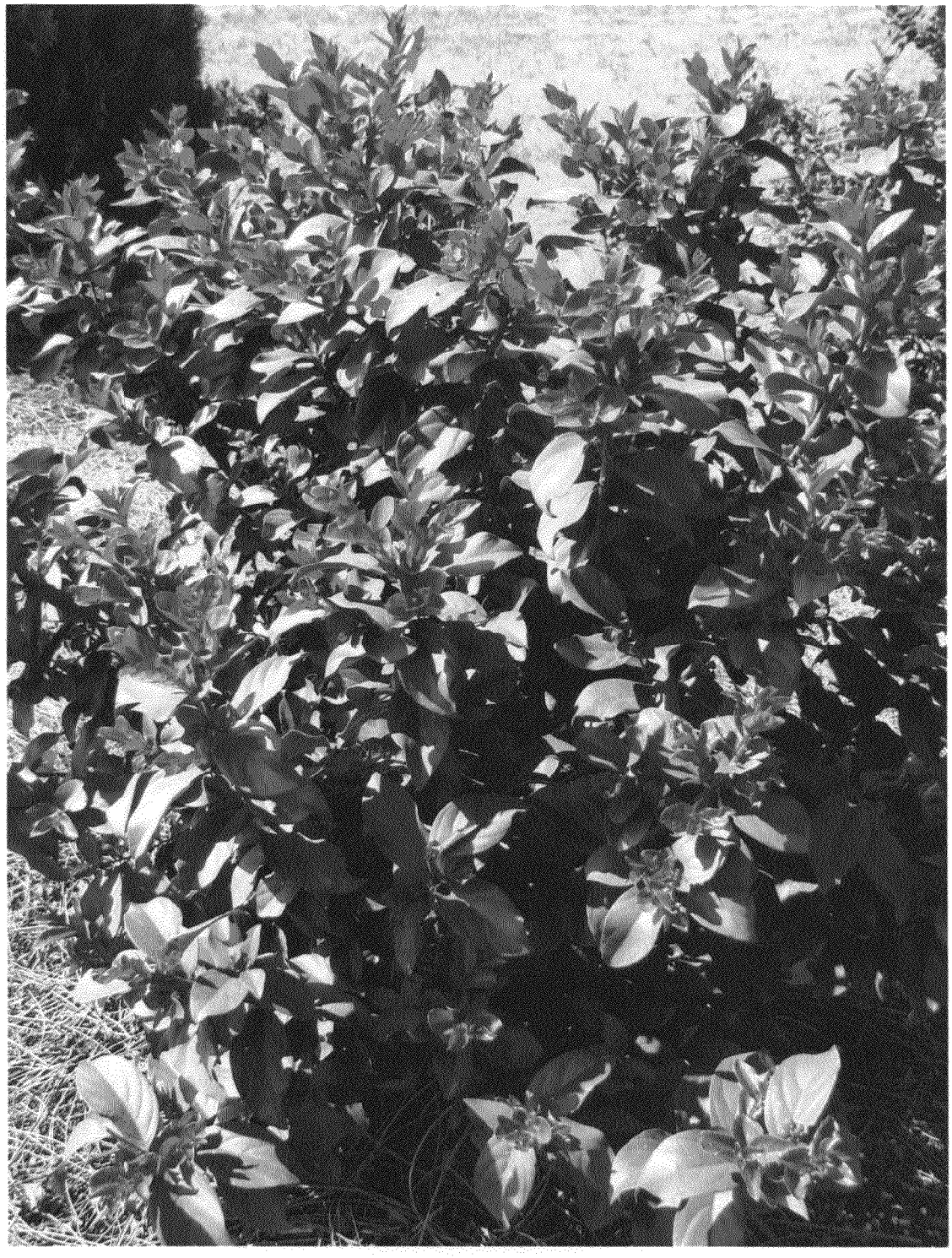
FIG. 3 illustrates the summer foliage and new growth of 'Plum Magic'.
Figure 4:
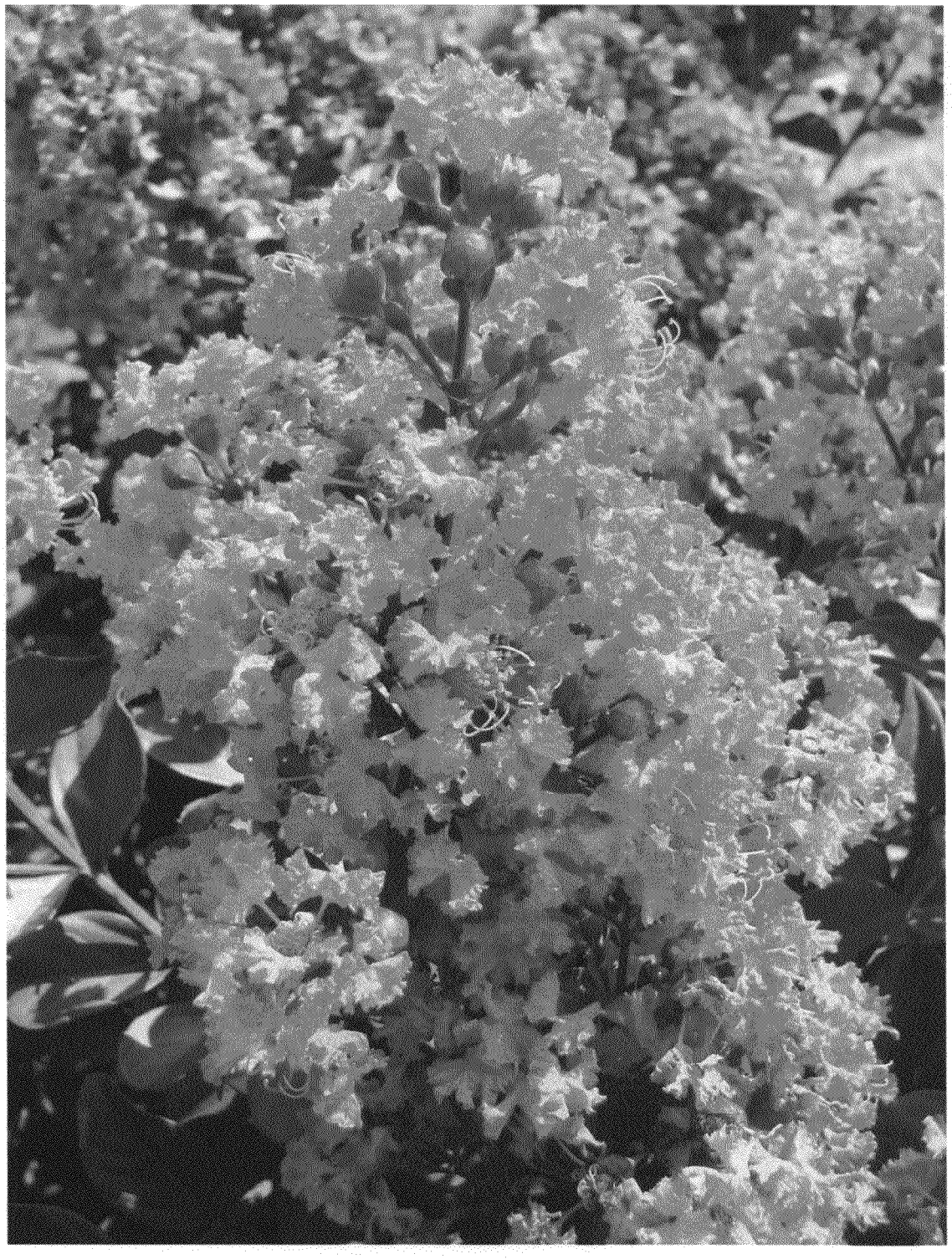
FIG. 4 illustrates a close-up view of the inflorescences of 'Plum Magic'.

In the following description, color references are made to The Royal Horticultural Society Colour Chart, 2001 Edition, except where general terms of ordinary dictionary significance are used. Plants used for the description were approximately two years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'Plum Magic'.

Parentage:

*Female, or seed, parent.*—*Lagerstroemia* 'Gamad VI' (U.S. Plant Pat. No. 22,161).

*Male, or pollen parent.*—Unknown (open-pollinated).

Propagation: Terminal cuttings.

Time to initiate roots, summer: About 21 days at 32° C.

Plant description: Flowering shrub; compact, rounded to upright growth habit. Freely branching; pruning enhances lateral branch development.

*Root description.*—Numerous, fine, fibrous and well-branched.

*Plant size.*—The original plant, now about four-years-old in the ground, is about 105 cm high from the soil level to the top of the inflorescences and about 95 cm wide.

*First year stems have a diameter of about 2 mm. Shape.*—Squarish.

*Second year and older stems have a diameter of about 5 mm or more. Shape.*—Round.

*Trunk diameter.*—2.5 cm at the soil line.

*Color.*—199A.

*Internode length.*—About 1.5 cm.

*Strength.*—Flexible when young, easily broken once mature.

*First year stem color* (*young*).—183A.

*Color* (*woody*).—199A.

*Second year and older stem color.*—N199D.

*Bark.*—Exfoliates in strips beginning on second or third year stems.

Vegetative buds: Sub-opposite to alternate in arrangement, imbricate, conical, with no pubescence.

*Color.*—183B.

*Size.*—About 2 mm in length and 1 mm in width.

Foliage description:

*Arrangement.*—Sub-opposite to alternate, simple.

*Length.*—About 4 cm.

*Width.*—About 2.2 cm.

*Shape.*—Elliptical.

*Apex.*—Acuminate.

*Base.*—Cuneate.

*Margin.*—Entire.

*Texture* (*upper and lower surfaces*).—Glabrous and glossy in developing foliage, and glabrous in fully expanded foliage.

*Venation pattern.*—Pinnate.

*Venation color of emerging foliage* (*upper surface*).—187A.

*Venation color of emerging foliage* (*lower surface*).—187C.

*Venation color of fully expanded foliage* (*upper surface*).—146C.

*Venation color of fully expanded foliage* (*lower surface*).—146D.

*Color in developing spring foliage* (*upper and lower surfaces*).—187A.

*Color in fully expanded summer foliage* (*upper surface*).—189A.

*Color in fully expanded summer foliage* (*lower surface*).—146B. Foliage color during the fall is 172C, 183C, or any combination of these colors.

*Petiole length.*—About 1 mm.

*Petiole diameter.*—About 1 mm.

*Petiole color* (*upper and lower surfaces*).—183B.

*Pubescence.*—None.

Flower description: Flowers are produced from about June to September in Watkinsville, Ga. An inflorescence is showy for about two weeks, and individual flowers last about one day and are self-cleaning.

*Inflorescence type.*—Panicle.

*Inflorescence length.*—About 11 cm.

*Inflorescence width.*—About 7 cm.

*Peduncle.*—About 9 cm in length, about 2 mm in diameter, color is 187A, and no pubescence.

*Individual flowers.*—About 2 cm by 3 cm.

*Flower buds.*—Length: about 7 mm; Diameter: about 6 mm; Color: 187B.

*Pedicels.*—About 8 mm in length, 59A in color, and no pubescence.

*Calyx.*—About 7 mm in length, about 7 mm in diameter, 183C in color, and no pubescence.

Petals:

*Arrangement/appearance.*—Usually 6 per flower.

*Petal length.*—About 1.5 cm.

*Petal width.*—About 1.2 cm.

*Petal shape.*—Fan-shaped.

*Petal apex.*—Ruffled, rounded.

*Petal base.*—Sagittate.

*Petal margin.*—Ruffled.

*Petal texture* (*upper and lower surfaces*).—Glabrous.

*Petal color.*—Upper and lower surfaces are 71B.

Stamens:

*Quantity/arrangement.*—About 20 to 25 short stamens clustered in the center, about 7 mm long, filament color is 11D, and anther color is 14A. The short stamens are surrounded by 6 longer stamens, about 1.2 cm long, filament color is 63A, and anther color is 22A. The stamens are not pubescent.

*Pollen.*—Produced in moderate quantities and is 13C in color.

Pistils:

*Quantity.*—One superior pistil per flower.

*Pubescence.*—None.

*Pistil length.*—About 1.5 cm in length.

*Stigma shape.*—Round, about 1 mm in diameter.

*Stigma color.*—166A.

*Style color.*—N34A and about 1 cm in length.

*Ovary color.*—10C and about 2.5 mm in diameter.

Fruit:

*Type/appearance.*—Six-valved, dehiscent, broad ellipsoidal capsule.

*Length.*—About 8 mm.

*Diameter.*—About 7 mm.

*Immature color.*—144A.

*Mature color.*—200C. Each capsule contains many seeds that are about 5 mm long, 3 mm wide, and 200C in color.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'Plum Magic', as illustrated and described herein.

* * * * *